United States Patent [19]

Wallace

[11] 4,209,392

[45] Jun. 24, 1980

[54] PORTABLE HEPATIC-ASSIST METHOD AND APPARATUS FOR SAME

[76] Inventor: Richard A. Wallace, 7304 SW. 53 Ave., Portland, Oreg. 97219

[21] Appl. No.: 905,956

[22] Filed: May 15, 1978

[51] Int. Cl.² .................. B01D 13/00; B01D 31/00
[52] U.S. Cl. .................. 210/23 F; 210/27; 210/321 B; 210/416 M; 128/DIG. 3
[58] Field of Search ............ 210/23 F, 321 B, 321 A, 210/416 M, DIG. 23, 27, 38 R, 40, 22, 266, 257 M, 314, 74; 128/DIG. 3

[56] References Cited

U.S. PATENT DOCUMENTS

| 3,579,441 | 5/1971 | Brown | 210/23 H |
|---|---|---|---|
| 3,608,729 | 9/1971 | Haselden | 210/321 |
| 3,799,873 | 3/1974 | Brown | 210/321 B |
| 3,827,975 | 8/1974 | Bizot et al. | 210/321 B |
| 3,979,284 | 9/1976 | Granger et al. | 210/22 A |
| 3,989,622 | 11/1976 | Marantz et al. | 210/22 R |
| 3,996,017 | 12/1976 | Kaiser | 210/31 C |
| 4,013,564 | 3/1977 | Nose | 210/434 |
| 4,024,059 | 5/1977 | Sausse | 210/195 R |

OTHER PUBLICATIONS

"A Combined Dialysis-Ion Exchange Resin Unit" J.S. McCaughan, Surgery, vol. 56 #4 Oct. 1964, pp. 750-756.
Juggi, Med. J. Aust., 1:926, 1973.
"Artificial Organs," Kolff, Trans. Am. Soc. Art. Int. Organs, vol. 23, 1977 pp. 1-11.
"Coated Adsorbents. . . " Andrade et al, Trans. Am. Soc. Art. Int. Organs, vol. 18, 1972 pp. 473-483.
"Artificial Support Systems . . . ," Perk et al, Cont. on Sorbents in Uremia and Hepatic Failure, 11/3/75.
"Hemo-Filtration-A New Method. . . " Quellhorst et al, Trans. Am. Soc. Art. Int. Ors. vol. 13, 1977 pp. 681-682.
"Third Generation Art. Kid. pH and Concentration Control" Trans. Am. Soc. Art. Int. Organs, Lai et al, 1975 vol. 21 pp. 346-351.

Primary Examiner—Thomas G. Wyse
Assistant Examiner—David R. Sadowski

[57] ABSTRACT

Portable hepatic-assist closed loop method and apparatus utilizing hemofiltration membrane and sterilizable disposable sorbents cartridge for adsorption of hepatic toxins.

8 Claims, 4 Drawing Figures

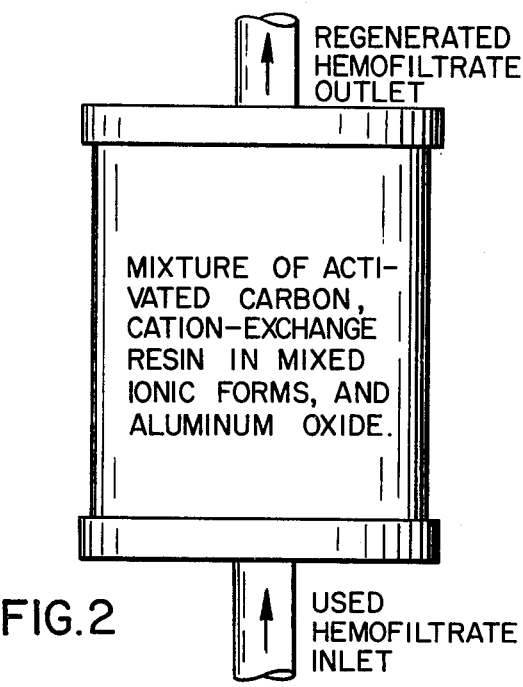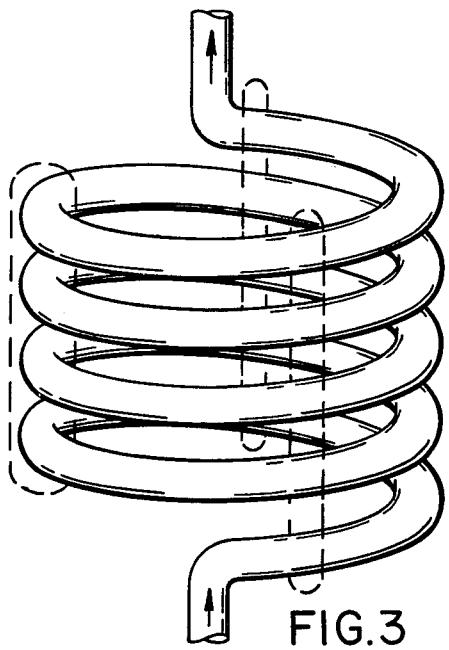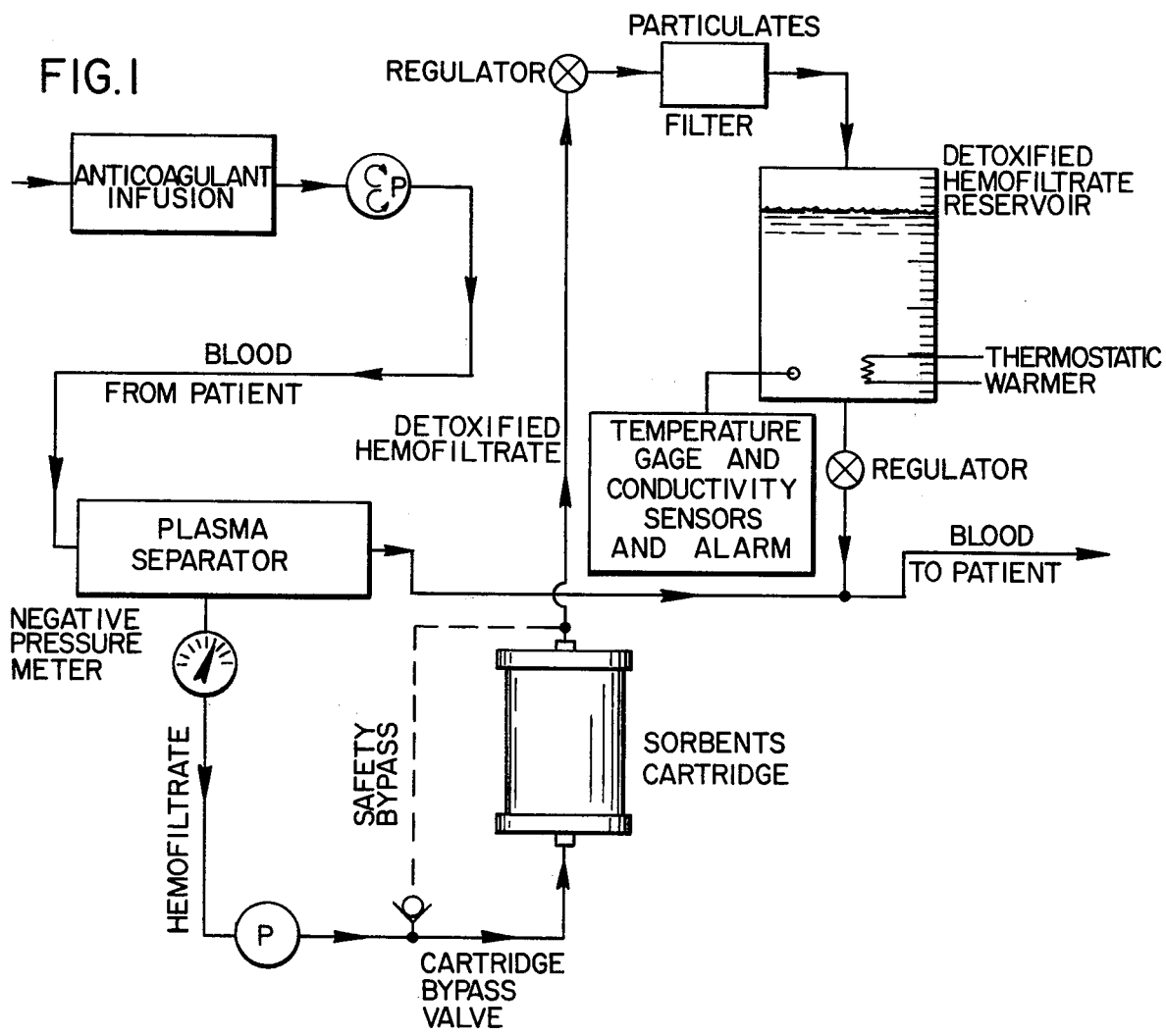

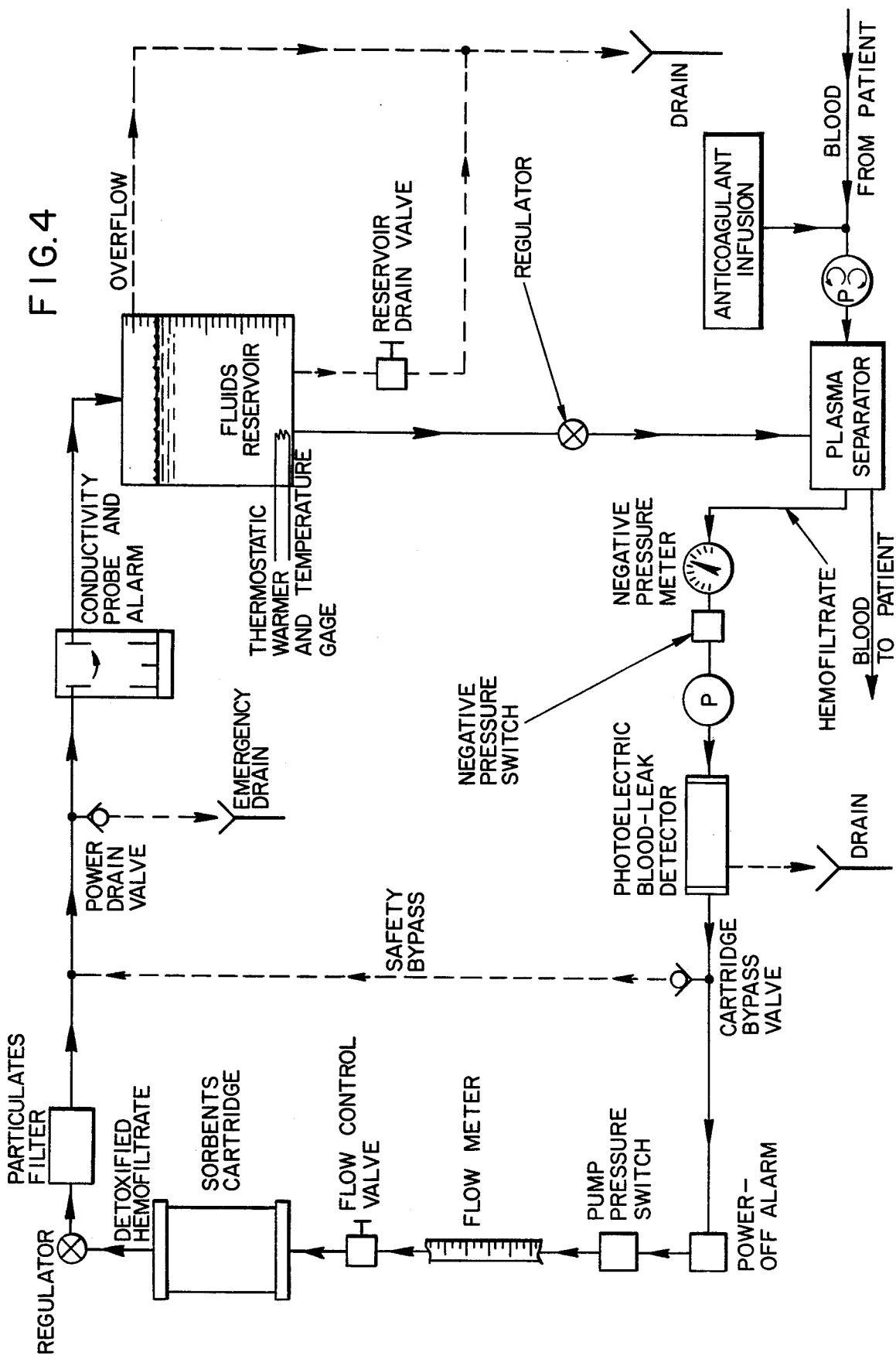

PORTABLE HEPATIC-ASSIST METHOD AND APPARATUS FOR SAME

BACKGROUND OF THE INVENTION

1. Field of the Invention

This invention relates to a hepatic-assist method and apparatus therefor. It relates particularly to a method and apparatus for removing hepatic toxins in cases of acute hepatic failure from human and animal blood. Most particularly, it relates to a novel hepatic-assist method and apparatus which is mechanically simple, portable, sterile and capable of removing virtually all hepatic toxins from human blood without substantial alteration of the blood's pH and electrolyte balance.

2. State of the Art

Various attempts have been made in recent years to remove hepatic toxins from blood by means of chemical sorbents.

One technique described by Juggi in Med. J. Australia, 1:926 (1973) comprises percolation of blood directly through a cation-exchange resin column, the resin being in its mixed sodium, potassium, calcium and magnesium forms. The described method has a number of drawbacks as a hepatic-assist system. Although effective in the removal of ammonium ion, critical hepatic toxins in the middle molecular weight range of 500 to 20,000 and excessive amino acids such as thyrosine and phenylalanine are not removed.

Another method of treating hepatic failure is by hemodialysis with high ultrafiltration rate membranes such as polyacrylonitrile, polycarbonate and anisotropic polysulfone membranes as described by Opolon et al in Trans. Amer. Soc. Artif. Int. 23:701 (1976). In this method, arterial blood from the comatose hepatic patient is connected to a polyacrylonitrile membrane hemodialyzer with a 50 liter closed loop, batch dialysate delivery machine. The dialysate is bicarbonate-based and sterile. Hepatic toxins are dialyzed out of the patient's blood while consequent fluid loss is made up by infused saline solution. Hemodialysis permits rapid removal of hepatic toxins which are extremely diluted in a large volume of dialysate fluid.

The method described by Opolon et al suffers from a number of disadvantages as well. A large volume (50 liters) of dialysate is needed which necessitates water purification systems and special plumbing as well as usage of bulky and expensive dialysate delivery machines. Because of the high volume of dialysate, the amount of body fluid removed cannot be measured accurately, let alone continuously during treatment, which often leads to excess fluid removal which in turn causes severe hypotension, unconsciousness and, in some cases, death. There is a significant loss of essential amino acids and vitamins from the patient due to their substantial dilution in the high volume of dialysate. Finally, the system is cumbersome and does not readily lend itself to bedside treatment.

Still another hepatic-assist method was recently reported by Maini et al in Amer. Soc. Artif. Int. Organs Abstracts, 6; 54 (1977). The reported in vitro technique uses recirculating dialysate comprising banked blood plasma which passes through a large, non-sterile column filled with ground anion-exchange resin, non-ionic resins, and activated carbon woven cloth. For high sorbent efficiency, usage of a finely ground sorbent is preferred by the authors. Bilirubin and bile acids are readily removed by the powdered anion-exchange resin. However, removal of ammonium hepatic toxin is not accomplished. Due to the inherently high pressure drop through a long column filled with considerable amounts of finely ground sorbents, admixed with woven sorbents cloths, the dialysate flow rate is necessarily low. Further, there is a possibility of microemboli formation from tiny sorbents fragments. In order for the treated plasma dialysate to be infused with incoming blood, a sterile column with sterilized sorbents must be used which is impractical with a bulky column and impossible to accomplish by radiation, autoclaving or gas sterilization due to chemical breakdown in the cases of radiation and autoclaving and contamination by adsorption in the case of gas sterilization.

SUMMARY OF THE INVENTION

It is a primary object of the present invention to provide a new and improved hepatic-assist method and apparatus.

Another object of this invention is to provide a portable hepatic-assist method and apparatus that removes essentially all hepatic toxins in a short period of time without substantial alternation of the normal blood pH and electrolyte balance.

A further object is to provide a hepatic-assist method and apparatus which allows continuous and accurate measurement and control of the volume of fluids removed from the patient when in operation and requires no infusate make-up of electrolytes.

A still further object is to provide a hepatic-assist method and apparatus which is clinically sterile, pyrogen-free, biocompatible and adjustable to the individual patient's pH and electrolyte levels.

These and other objects as well as the manner of achieving them will become apparent to those skilled in the art from the detailed description and accompanying drawings which follows.

According to the present invention, an automatic portable haptic-assist method and apparatus is provided by a low volume, closed-loop hemofiltration system which utilizes a hemofiltration membrane device and pre-equilibrated sorbents-regenerated hemofiltrate. Fluid containing substantially all hepatic toxins from the blood, constituting a hemofiltrate, is removed from the blood by a biocompatible hemofiltration membrane device and passed through a sterilizable disposable sorbents cartridge containing activated charcoal, strong acid cation-exchange resin and aluminum oxide, which removes essentially all hepatic toxins from the hemofiltrate. The strong acid cation-exchange resin contains only calcium, sodium and potassium electrolytes in pre-equilibrated amounts so that no electrolyte make-up infusate is required. Surprisingly, it was found that the level of magnesium in the blood was independent of the presence of magnesium in the cation-exchange resin, thus rendering its presence in the resin unnecessary. The amount of fluid removal from the patient is accurately and continuously measurable. After passing through the sorbents cartridge, the detoxified hemofiltrate may be automatically heated to body temperature, checked for proper pH and total electrolyte level, and either returned to the patient's blood or recirculated in the closed loop hemofiltrate circuit.

BRIEF DESCRIPTION OF THE DRAWINGS

FIG. 1 is a schematic flow diagram of the preferred embodiment of the portable hepatic-assist hemofiltration system according to the present invention.

FIG. 2 is a sectional schematic view of a sorbents cartridge according to the present invention.

FIG. 3 is a perspective view showing another embodiment of a sorbents cartridge according to the present invention.

FIG. 4 is a schematic flow diagram of another embodiment of the portable hepatic-assist hemofiltration system according to the present invention.

DETAILED DESCRIPTION OF THE INVENTION

Referring to the drawings FIGS. 1-4, and specifically to FIG. 1, which illustrates the preferred embodiment, arterial blood is pumped from the patient by means of a Scribner shunt and a suitable blood pump such as a roller pump, infused with an anti-clotting composition such as heparin, and passed through a conventional hemofiltration membrane plasma separator such as an Amicon capillary filter Model No. XM50 wherein fluid containing substantially all hepatic toxins is rapidly removed from the arterial blood by convective transport, thereby forming a hemofiltrate. The hemofiltration membrane plasma separator contains a number of high porosity ultrafiltration microporous membranes with an average pore diameter on the order of 0.1 to 0.5 micron and from about 5 to about 50 microns in thickness and may be employed in sheet, hollow fiber, or hemicapillary forms. Examples of suitable membranes are the polyacrylonitrile "AN-69" made by Rhone-Poulenc, polycarbonate manufactured by C. R. Bard, Inc., microporous cellulosic membranes such as cellulose triacetate, manufactured by Sartorious Goettinger, polymethylmethacrylate manufactured by Torray Industries, polypropylene manufactured by Celanese Corporation and polysulfone manufactured by Amicon. Transmembrane pressure sufficient to cause passage of the fluid containing hepatic toxins is on the order of 200-600 mm Hg, created by the roller blood pump and a negative pressure pump on the other side of the plasma separator.

Hepatic toxins such as ammonium ions, excess amino acids such as thyrosine and phenylalanine, lipids, bile acids or salts, free fatty acids, bilirubin-bound protein and organic middle molecular weight toxins ranging in molecular weight from 500 to 20,000 readily pass through the highly porous semipermeable membrane and into the hemofiltrate.

Two embodiments of the sorbents cartridge are shown in FIGS. 2 and 3. That shown in FIG. 2 is a conventional filter-type cartridge with port inlets and outlets filled with a mixture of activated carbon, a strong acid cation-exchange resin such as a polysulfonate or phenolic-type resin in its mixed calcium, sodium and potassium forms, while that shown in FIG. 3 is the preferred embodiment, which is helically-wound hollow tubing which may be clamped with a clamp or fastener (shown by dotted lines) and filled with the same mixture. The precise toxins responsible for acute hepatic failure are unknown; aluminum oxide or magnesium oxide or mixtures thereof may also be used in the sorbents mixture if bile acids or salts, free fatty acids, and bilirubin are to be removed from the hemofiltrate.

The sorbents mixture can be prepared by any suitable means so long as the approximate composition by weight is from 20 to 70% activated charcoal, 25-85% cation-exchange resin in its mixed ionic forms (10 to 35% being in the sodium form, 15 to 40% in the calcium form and 1 to 10% in the potassium form), and 0 to 30% aluminum oxide. One method of preparation involves separately washing activated charcoal and sodium form polysulfonate cation-exchange resin, both in the 16-50 mesh range, with deionized water and converting a portion of the sodium form to the calcium or potassium form by separate treatment with a saturated calcium or potassium chloride solution. Air-dried resin in the sodium and potassium forms weighing about 0.5 kg (approximately 40% by weight in sodium form, 57% in calcium form, and 3% in potassium form), is mixed with activated charcoal and aluminum oxide so that the final weight percentage composition is approximately 20.5% sodium, 28.5% calcium, 1% potassium, 40% activated charcoal and 10% aluminum oxide. Ratios may, if desired, be varied to within 10% so as to meet the individual serum requirements of the patient. The sorbents are intermixed and transferred to the cartridge and then irrigated with a standard bicarbonate-based physiological salts solution. To obtain a sterile hemofiltrate, the pre-equilibrated sorbents cartridge is autoclaved at 121° C. for ½ hour and the inlet and outlet ports are sealed until the cartridge is ready for use. Alternatively, radiation or chemical sterilization, such as with the use of formalin, can be used.

If desired, the individual cationic concentration of the hemofiltrate electrolytes can be altered in the cation-exchange resin ionic ratio in order to adjust to a given patient's excesses or deficiencies of calcium, potassium and sodium levels in the blood. For example, the calcium level could be adjusted so as to yield a calcium hemofiltrate concentration level of 4.0, 3.5 or 3.0 mEq/L. Other agents, such as sterile amino acids and vitamins may be readily added directly to the detoxified hemofiltrate.

As noted above, the preferred sorbents cartridge is that shown in FIG. 3, which is less susceptible to channeling during operation. A dry mixture of the activated charcoal, cation-exchange resin in its mixed calcium, sodium and potassium forms and aluminum oxide as prepared above is placed together in the tubing and subjected to vibration so as to insure dense packing, then mechanically pressure-sealed with plugs provided with ¼ inch ports at both ends.

In use, the outlet line of the sorbents cartridge is clamped shut for a few minutes to fill it with hemofiltrate in order to expel any air present, permit the particles to swell and provide a backwash so as to minimize channeling. A single cartridge prepared as above is capable of detoxifying 10 to 20 liters of blood, depending upon individual toxicity.

After passing through the semipermeable membranes of the plasma separator, the fluid portion of arterial blood containing the hepatic toxins is incorporated into and constitutes part of the hemofiltrate. The hemofiltrate is thereafter pumped through the sorbents cartridge wherein essentially all of the hepatic toxins are removed without substantial alteration of the cationic concentration and pH levels of the detoxified hemofiltrate. Ammonium ion and trace amounts of aluminum and heavy metals (when present) such as lead, mercury, uranium, zirconium and copper, are adsorbed on the cation-exchange resin while lipids, amino acids, phenolic substances, mercaptans and organic middle molecular weight molecules are adsorbed by the activated charcoal. Free fatty acids, bile acids or salts, and bilirubin are removed by the aluminum oxide. Thereafter, the detoxified hemofiltrate is filtered through an extremely fine submicron particulates filter via a conventional adjustable valve regulator to remove any bacteria, pyrogens and sorbents fines which could lead to the formation of microemboil and passed to a detoxified hemofiltrate reservoir wherein the concentration of the electrolyte level present in the hemofiltrate may be measured by conventional electroconductivity measuring means such as a flow-type conductivity cell sensor and the hemofiltrate is warmed to the appropriate temperature (about 37° C.) by a small thermostatic warmer before recombining with the blood and returned via a conventional adjustable valve regulator to the patient intravenously. The conductivity sensor is connected to an audio/visual alarm so as to alert the operator in the event that the hemofiltrate electrolyte levels deviate from permissable norms.

The detoxified hemofiltrate reservoir has a portion thereof marked with a suitable graduated volumetric index whereby the actual hemofiltrate fluid level, which is the amount of body fluid removed from the patient, can be directly and continuously visually monitored, as opposed to calculated as in prior art devices utilizing large volumes of dialysate. The total fluid volume of the apparatus is on the order of only 4–8 liters, the reservoir having the major portion of the volume.

Referring to FIG. 4, another embodiment of the present invention is shown that combines convective transport with controlled diffusive transport using the same type of conventional hemofiltration plasma separator discussed above, wherein the detoxified hemofiltrate may be either maintained in an extracorporeal closed loop circuit or returned directly to the patient. This embodiment provides a higher rate of removal of the lower (below 500) molecular weight hepatic toxins, such as ammonium ions, amino acids, bile salts, etc.

In general, a positive pressure in the range of 200 to 300 mm Hg on the blood side of the membrane and a negative pressure on the hemofiltrate side of the membrane device is imposed, resulting in about 300 to 500 mm Hg transmembrane pressure, which generates on the order of 40 to 90 ml of hemofiltrate per minute. With a blood flow rate of 150 ml/min and a detoxified hemofiltrate recirculation rate of 200 ml/min, about 60 ml/min of organic middle molecular weight toxins as well as about 140 ml/min ammonium, about 140 ml/min amino acids such as thyrosine and phenylalanine and about 120 ml/min bile acids are removed during a 3 hour treatment.

Arterial blood is pumped from the patient by means of a Scribner shunt and a blood pump such as a roller pump, infused with an anti-clotting composition, and passed to the same sort of conventional hemofiltration plasma separator device discussed in connection with FIG. 1. The hemofiltrate obtained from the hemofiltration device may pass through a negative pressure meter, microswitch, negative pressure pump and photoelectric blood leak detector into a closed loop containing a small amount, on the order of 3–6 liters, of recirculating sterile physiological salts solution.

The physiological salts solution is an aqueous solution of the known physiological salts of calcium, sodium, potassium and magnesium, which can be, for example, a modified Ringer's solution, and is used as a carrier in the recirculating hemofiltrate loop. For better correction of the acid-base imbalance and increased patient tolerance to rapid hemofiltration, a bicarbonate or acetate/bicarbonate-based physiological salts solution may be employed, the former being preferred. A typical bicarbonate-based physiological salts solution composition is 97 mEq/L NaCl, 35 mEq/L NaHCO$_3$, 3.5 mEq/L CaCl$_2$, 1.5 mEq/L MgCl$_2$ and 2.0 OmEq/L KAc. Several more equivalents of acetic acid may be added to maintain the pH at or below 7.4, the normal physiological pH level.

The negative pressure meter, microswitch and pump may be connected so that when the pressure in the system drops below a pre-set pressure, the switch shuts off the pump.

The hemofiltrate is passed through the same type of sorbents cartridge described above whereby hepatic toxins are adsorbed. The detoxified hemofiltrate passes through a particulates filter which removes particles which may be released from the sorbents cartridge. The filter for the embodiment shown in FIG. 4 need not be as fine as that shown in FIG. 1 since the recirculating hemofiltrate never comes into direct contact with the blood of the patient, always being separated therefrom by the membranes in the plasma separator. The detoxified hemofiltrate thereafter optionally passes by a power drain valve which is activated in an emergency such as a drop in pressure in the system, through a conductivity probe which measures the total concentration of salts present in the hemofiltrate by conventional electroconductivity measuring means such as a flow-type conductivity cell sensor. The probe activates an alarm should the electrolyte concentration fall below acceptable levels.

The detoxified hemofiltrate then passes to a fluids reservoir which preferably contains the major portion of the physiological salts solution and the same sort of graduated volumetric index marked thereon as discussed above, the total fluid volume of the apparatus being about 4–8 liters. The amount of fluid removed from the patient's body is ascertainable by simply noting the difference in fluid level taken at the time of the reading and prior to commencement of hemofiltration. By using a relatively low volume of physiological salts solution, on the order of 3–6 liters, the amount of body fluids removed in a given treatment period, which is usually on the order of 2 liters or less, appears as a significant increment over the amount of physiological salts solution initially present and so is directly measurable to a degree of accuracy not heretofore obtainable with large volume hemofiltration systems.

The fluid in the reservoir may be thermostatically warmed to the proper temperature and monitored by a conventional temperature gauge. For purposes of draining and sterilizing the system, the reservoir is preferably provided with a drain valve. Optionally, the reservoir may be provided with an overflow means as long as it is so arranged as to maintain a closed loop in the system.

From the reservoir, the detoxified hemofiltrate, now mixed with the physiological salts solution, is returned, via an adjustable valve regulator, to the closed loop via the hemofiltration device wherein it takes on additional hepatic toxins from the patient's arterial blood and is again subjected to detoxification by adsorption in the sorbents cartridge.

A disinfecting cycle of the apparatus of the present invention may be automatically activated by circulating a suitable chemical disinfectant solution or hot (92° C.)

water, at a flow rate of about 200 ml/min for about 20 minutes. The used sorbents cartridge and particulates filter are discarded.

Hemofiltrate temperature may be regulated by a high limit alarm. Arterial and venous line pressures may be constantly monitored by adjustable high and low limit alarms. If these pressure levels are exceeded, the power is automatically turned off to the blood pump.

Overall system monitoring for blood leaks, temperature, transmembrane pressure, total system pressure, total electrolyte, and pH level and disinfection in the method and apparatus of the present invention can be coordinated by the use of a simplified integrated component electronic circuit such as is commercially available in the form of a microcomputer.

EXAMPLE 1

In-vitro test results with a single sorbents cartridge show that the cation-exchange resin mixture, in its pre-equilibrated salt forms as described above, removed 1.8 mg of ammonium per gram of resin at a concentration of 3.2 mg % ammonium. Further, the alumina portion of the sorbents mixture adsorbed 0.021 millimoles of free fatty acids, 2.5 mg of bilirubin at a concentration of 7 mg %, as well as 0.030 millimoles of bile salts and acids. The flow rate of the synthetic physiological salts solution containing known amounts of the above hepatic toxin substances was 70 ml/min at 37° C. This solution was allowed to pass upwards through the type of sorbents cartridge shown in FIG. 3 containing activated charcoal, 16–25 mesh cation-exchange resin in its mixed ionic forms, and alumina in 30%, 50%, and 20% respectively, by weight, the resin being about 40% by weight in the sodium form, 57% in the calcium form, and 3% in the potassium form.

EXAMPLE 2

The portable hepatic-assist apparatus shown in FIG. 1 comprises, in significant part, a conventional roller blood pump which draws arterial blood from the forearm of the patient by a Scribner shunt; a syrine-type anticoagulant infusion means, whereby heparin is infused into the arterial blood; a hemofiltration membrane plasma separator comprising an Amicon capillary filter membrane device, Model No. XM50, which utilizes a series of polysulfone hollow fiber membranes about 30 microns in thickness with a pore diameter in the range of about 0.2–0.4 micron; a negative pressure meter; a finger pump; a helically-wound sorbents cartridge as shown in FIG. 3 and prepared as discussed above containing 16–50 mesh activated charcoal, a pre-equilibrated cation-exchange resin and aluminum oxide, in 40%, 50% and 10% respectively by weight, the cation-exchange resin being about 40% by weight in the sodium form; an adjustable valve regulator; a continuous-flow bacteria particulates filter removing submicron particles on the order of 0.1–0.2 micron; a hemofiltrate reservoir comprising a 5 liter polypropylene vessel, a low-wattage thermostatic warmer with a thermistor and a conventional flow-type electroconductivity sensor inserted therein connected to an audio-visual alarm; and a standard in-line by-pass valve.

Utilizing the apparatus described above, hemofiltrate is continuously detoxified through the sorbents cartridge. The flow rate is adjusted to 40–60 ml per min by gradually adjusting the transmembrane pressure differences on either side of the plasma separator membrane to a total transmembrane pressure differential of 325 mm Hg. Detoxified sterile hemofiltrate is returned to the venous bloodline by the intravenous portion of the Scribner shunt at a flow rate of 30–40 ml/min. Ammonium level is markedly reduced from an initial 3840 micrograms per 100 ml to about 15 micrograms per 100 ml in three hours of hemofiltration. The bilirubin level of 23 milligrams per 100 ml was reduced to about 3.5 milligrams per 100 ml. Other hepatic toxins, including free fatty acids, bile acids, tyrosine and phenylalanine, lipids, mercaptans, and phenols are also removed from the blood stream by adsorption on the sorbents cartridge. Calcium, sodium and pH levels are maintained substantially constant throughout the hemofiltration by the pre-equilibrated bicarbonate-based sorbents cartridge.

EXAMPLE 3

Example 2 is repeated using a series of dry polycarbonate hemofiltration membranes produced by C. R. Bard, Inc. about 21.6 microns in thickness and with a pore diameter in the range of 0.2–0.5 micron; one square meter of membrane surface area with ann ultrafiltration rate of 15.6 ml/hr/mm Hg is used. Similar results to those obtained in Example 2 are achieved.

EXAMPLE 4

Example 2 is repeated using a number of Celgard 3501 polypropylene membranes by Celanese Corporation about 10 microns in thickness with an average pore diameter of about 0.4 micron. Similar results to those in Example 2 are obtained.

EXAMPLE 5

Example 2 is repeated with the use of 6 sheets of cellulose triacetate hemofiltration membrane manufactured by Sartorious Goettingen of West Germany, with a thickness of 16 microns and a pore diameter in the range of 0.1–0.4 micron. Such a membrane device rapidly removes bilirubin, bile acids, free fatty acids and other protein-bound substances. Bilirubin-bound albumin is adsorbed in the sorbents cartridge, showing a concentration of less than 0.2 mg % in comparison to 6.2 mg % prior to treatment. Blood serum data shows a marked decrease in blook bilirubin, bile acids, glucose, mercaptans and ammonium ion, with no change in serum alkaline phosphates, and lactic dehydrogenase.

EXAMPLE 6

Example 2 is repeated with the use of a Filtryzer polymethylmethacrylate hollow fiber membrane device by Torray Industries containing a bundle of 9500 fibers, with an internal diameter of 240 microns, a wall thickness of 40 microns with pores through the walls in the range of about 0.08–0.15 micron and an internal surface area of 1.36 square meters. The hemofiltrate obtained from the plasma separator is pumped upwards through the sorbents cartridge at a rate of 40 ml/min. Blood ammonium level is reduced from 8600 micrograms per 100 ml to about 10 micrograms per 100 ml or 0.01 mg %. The detoxified hemofiltrate shows a calcium level of 3.6 mEq/L and a potassium level of 1.8 mEq/L with no substantial change in the 3 hour period of treatment. Periodic pH measurements during hemofiltration show that the pre-equilibrated bicarbonate buffer in the sorbents cartridge compensates for an acidotic condition. No excess of any of phenylalanine, tryptophan, and methionine is found in the detoxified hemofiltrate. There is a marked decrease in serum bilirubin, a substantial portion thereof being adsorbed in the sorbents cartridge.

EXAMPLE 7

The portable hepatic assist apparatus shown in FIG. 4 comprises a Rhone-Poulenc Model No. 6 dialyzer as a hemofiltration membrane plasma separator with a polyacrylonitrile series of membranes about 25 microns in thickness with an average pore diameter in the range of about 0.1–0.2 micron; a negative pressure meter; a Drake-Willock negative pressure pump; a photoelectric blook leak detector connected to a drain; a cartridge bypass valve; power-off alarm switch; a pump pressure switch; an adjustable flow control valve; a sorbents cartridge of the type shown in FIG. 3 containing 20–50 mesh activated charcoal, a pre-equilibrated cation-exchange resin prepared in the same ratios and in the same manner as in Example 2 in the sodium, calcium and potassium forms and aluminum oxide; an adjustable valve regulator; an in-line conventional particulates filter filtering particles on the order of 1–2 microns; an electrical power drain valve for emergency draining; a flow-type conductivity probe and audio/visual alarm; an 8 liter polypropylene fluids reservoir containing a modified Ringer's solution containing sodium, potassium and calcium concentrations of 138 mEq/L 2.0 mEq/L, and 3.8 mEq/L at a physiological pH of 7.40; and a low-wattage thermostatic warmer with a thermistor and temperature sensor.

Utilizing the apparatus described above with 5.5 liters of the modified Ringer's solution recirculating at a flow rate of 400 ml/min, the hemofiltrate is continuously regenerated in a closed loop by adsorption in the sorbents cartridge for a period of about 3 hours. Average blood flow is 200 ml/min with a hemofiltration rate of 20 ml/min and a transmembrane pressure of approximately 400 mm Hg.

Biochemical analysis of the hepatic blood shows an initial ammonium level of 3800 micrograms/100 ml. After 3 hours of treatment, the blood ammonium level is decreased to about 33 micrograms/100 ml. The pre-serum calcium and magnesium levels of 4.9 and 1.8 mEq/L remain relatively unchanged at post-serum calcium and magnesium concentrations of 5.2 and 1.8 mEq/L, respectively. Pre-serum potassium and sodium levels of 4.1 and 133 mEq/L respectively also are not significantly altered relative to those for postserum potassium and sodium, being 4.0 and 137 mEq/L, respectively. Similarly, the initial and final calcium, potassium and sodium concentration in the detoxified hemofiltrate of 3.5, 2.0 and 140 mEq/L, respectively, is not changed significantly.

Ammonium levels in the hemofiltrate are effectively bound by the cation-exchange resin in the sorbents cartridge, remaining at about the normal physiological level of 0.3 mg % during treatment.

Bile acids, such as hexanoic, oleic and octanoic acids, as well as excess free fatty acids are found to be removed from the blood. No bilirubin or albumin is detected in the detoxified hemofiltrate. Excess amino acids, such as thyrosine and phenylalanine, phenols, mercaptans, organic middle molecular weight substances with an average molecular weight of from 500 to 20,000 and lipids, including triglycerides, cholesterol esters, and short-chain fatty acids are also adsorbed by the sorbents cartridge. Usage of 35 mEq/L of bicarbonate eliminates the acidosis problem and prevents large shifts in serum pH levels.

EXAMPLE 8

Example 7 is repeated, using 4.0 liters of the same bicarbonate-based physiological salts solution recirculated at a rate of 250 ml/min. An average blood flow rate of 150 ml/min is maintained for about 3 hours with similar results.

The nature, scope, utility, and effectiveness of the present invention have been described and specifically exemplified in the foregoing specification. The terms and expressions which have been employed in the foregoing abstract and specification are used therein as terms of description and not of limitation, and there is no intention, in the use of such terms and expressions, of excluding equivalence of the features shown and described on portions thereof, it being recognized that the scope of the invention is defined and limited only by the claims which follow.

What is claimed is:

1. A process for removing hepatic toxins from blood comprising forming a hemofiltrate by passing the blood adjacent to microporous membranes having an average pore diameter of from about 0.1 to about 0.5 micron, and causing a pressure differential across said membranes such that a fluid portion of the blood containing substantially all hepatic toxins passes through the membranes, thereby forming a hemofiltrate, and contacting said hemofiltrate with a sterilizable 16–50 mesh sorbents mixture consisting essentially of activated charcoal and a pre-equilibrated strong acid cation-exchange resin in mixed sodium, calcium and potassium forms, the sorbents mixture containing by weight, 20–70% activated charcoal, 25–85% cation-exchange resin and 0–30% by weight aluminum oxide, and the cation-exchange resin containing, by weight, 10–35% in the sodium form, 15–40% in the calcium form and 1–10% in the potassium form.

2. A process for removing hepatic toxins from blood comprising forming a hemofiltrate by passing the blood adjacent to microporous membranes having an average pore diameter of from about 0.1 to about 0.5 micron, and causing a pressure differential across said membranes such that a fluid portion of the blood containing substantially all hepatic toxins passes through the membranes, thereby forming a hemofiltrate, contacting said hemofiltrate with a sterilizable sorbents mixture consisting essentially of activated charcoal and a pre-equilibrated strong acid cation-exchange resin in mixed sodium, calcium and potassium forms, the sorbents mixture containing, by weight, 20–70% activated charcoal, 25–85% cation-exchange resin and 0–30% by weight aluminum oxide, and the cation-exchange resin containing, by weight, 10–35% in the sodium form, 15–40% in the calcium form and 1–10% in the potassium form, diluting said hemofiltrate with a volume of physiological salts solution of between 3 and 6 liters, and continuously recycling said diluted hemofiltrate adjacent said membranes and through said sorbents mixture.

3. The process of claims 1 or 2 wherein the microporous membranes are made of a material selected from the group consisting of polyacrylonitrile, polycarbonate, cellulose, triacetate, polymethylmethacrylate, polypropylene and polysulfone.

4. A closed loop portable hepatic-assist apparatus comprising, in combination:

(a) first conduit means for coupling a human artery to plasma separator means;

(b) plasma separator means comprising a series of microporous membranes having an average pore diameter of from about 0.1 to about 0.5 micron, which, under the influence of sufficent transmembrane pressure, will permit passage of a fluid portion of arterial blood containing substantially all hepatic toxins, thereby forming a hemofiltrate, and not permit passage of the remainder of said blood;

(c) first pump means and said plasma separator means for pumping arterial blood to said plasma separator means;

(d) second conduit means for returning the remainder of said blood which does not pass said microporous membranes to a human vein;

(e) sterilizable sorbents contacting means for contacting said hemofiltrate and adsorbing hepatic toxins, thereby forming a detoxified hemofiltrate comprising containing means for containing a 16-50 mesh sorbents mixture of activated charcoal and pre-equilibrated strong acid cation-exchange resin in mixed sodium, potassium and calcium forms, said sorbents mixture containing, by weight, 20-70% activated charcoal, 25-85% cation-exchange resin and 0-30% by weight aluminum oxide, and the cation-exchange resin containing, by weight, 10-35% in the sodium form, 15-40% in the calcium form and 1-10% in the potassium form;

(f) third conduit means for conveying said hemofiltrate to said sorbents contacting means;

(g) first regulator means for controlling the flow of said detoxified hemofiltrate;

(h) filtering means for removing bacteria, pyrogens and submicron particulates from said detoxified hemofiltrate;

(i) reservoir means for receiving said detoxified hemofiltrate;

(j) second pump means for pumping said detoxified hemofiltrate from the plasma separator means to the detoxified hemofiltrate reservoir means via said third conduit means, said sorbents contacting means, said first regulator means and said filtering means;

(k) fourth conduit means for conveying said detoxified hemofiltrate from said reservoir means to said second conduit means; and (l) second regulator means disposed within said fourth conduit means for controlling the flow of said detoxified hemofiltrate from said reservoir means to said second conduit means.

5. A closed-loop portable hepatic-assist apparatus comprising, in combination:

(a) first conduit means for coupling a human artery to plasma separator means;

(b) plasma separator means comprising a series of microporous membranes having an average pore diameter of from about 0.1 to about 0.5 1 micron, which under the influence of sufficient transmembrane pressure, will permit passage of a fluid portion of arterial blood containing substantially all hepatic toxins, thereby forming a hemofiltrate, and not permit passage of the remainder of said blood;

(c) first pump means disposed between said first conduit means and sid plasma separator means for pumping arterial blood to said plasma separator means;

(d) second conduit means for returning the remainder of said blood which does not pass said microporous membranes to a human vein;

(e) sterilizable sorbents contacting means for contacting said hemofiltrate and adsorbing hepatic toxins, thereby forming a detoxified hemofiltrate 16-50 mesh sorbents mixture of activated charcoal and pre-equilibrated strong acid cation-exchange resin in mixed sodium, potassium and calcium forms, said sorbents mixture containing, by weight, 20-70% activated charcoal, 25-85% cation-exchange resin and 0-30% by weight aluminum oxide, and the cation-exchange resin containing, by weight, 10-35% in the sodium form, 15-40% in the calcium form and 1-10% in the potassium form;

(f) third conduit means for conveying said hemofiltrate to said sorbents contacting means;

(g) first regulator means for controlling the flow of said detoxified hemofiltrate;

(h) filtering means for removing particulates from said detoxified hemofiltrate;

(i) reservoir means for containing a physiological salts solution and for receiving sid detoxified hemofiltrate;

(j) second pump means for pumping said detoxified hemofiltrate from the plasma separator means to the detoxified hemofiltrate reservoir means via said third conduit means, said sorbents contacting means, said first regulator means and said filtering means;

(k) fourth conduit means for returning said detoxified hemofiltrate and said physiological salts solution from said reservoir means to said pfasma separator means; and (l) second regulator means disposed within said fourth conduit means for controlling the flow of said detoxified hemofiltrate and said physiological salts solution from said reservoir means to said plasma separator means.

6. The apparatus of claim 4 or 5 wherein the containing means of the sorbents contacting means comprises helically-wound hollow tubing.

7. The apparatus of claims 4 or 5 wherein the reservoir means has a volumetric index to indicate the volume of fluid removed from the arterial blood.

8. The apparatus of claims 4 or 5 wherein the total fluid volume capacity of the apparatus is from 4-8 liters.

* * * * *